United States Patent [19]
el Kouni et al.

[11] Patent Number: 5,721,241
[45] Date of Patent: Feb. 24, 1998

[54] ENZYME INHIBITORS, THEIR SYNTHESIS, AND METHODS FOR USE

[75] Inventors: Mahmoud H. el Kouni; Fardos N. M. Naguib, both of 4632 Round Forest Dr., Mt. Brook, Ala. 35213-1832; Raymond F. Schinazi, 1524 Regency Walk Dr., Decatur, Ga. 30033

[73] Assignees: Mahmoud H. el Kouni; Fardos N. M. Naguib, both of Mt. Brook, Ala.; Raymond F. Schinazi, Atlanta, Ga.

[21] Appl. No.: 466,470

[22] Filed: Jun. 6, 1995

Related U.S. Application Data

[62] Division of Ser. No. 146,838, Nov. 2, 1993, Pat. No. 5,476,855.

[51] Int. Cl.$^6$ .................... A61K 31/505; C07D 239/02
[52] U.S. Cl. .................... 514/269; 514/270; 514/274; 544/300; 544/301; 544/302; 544/303; 544/310; 544/311; 544/314
[58] Field of Search ................. 544/300, 301, 544/302, 303, 310, 311, 314; 514/269, 270, 274

[56] References Cited

U.S. PATENT DOCUMENTS

| | | | |
|---|---|---|---|
| 3,687,931 | 8/1972 | Verheyden et al. | 260/211.5 |
| 3,755,295 | 8/1973 | Verheyden et al. | 260/211.5 R |
| 4,415,573 | 11/1983 | Ochi et al. | 424/251 |
| 4,613,604 | 9/1986 | Chu et al. | 514/274 |
| 4,868,187 | 9/1989 | Ogilivie | 514/269 |
| 5,077,280 | 12/1991 | Sommadossi et al. | 514/69 |
| 5,112,835 | 5/1992 | Miyasaka et al. | 544/302 |
| 5,141,943 | 8/1992 | Naguib et al. | 514/270 |
| 5,318,972 | 6/1994 | Miyasaka et al. | 514/269 |
| 5,476,855 | 12/1995 | El Kouni et al. | 514/269 |

OTHER PUBLICATIONS

Wasternack, *Pharmac. Ther.*, 8:629–651 (1981).
Naguib, et al, *Cancer Res.*, 45:5405–5412 (1985).
Harris, et al, *Biochem. Pharmac.*, 37:4759–4762 (1988).
Harris, et al, *Cancer Res.*, 49:6610–6614 (1989).
Nauib, et al, *Biochem Pharmac.*, 45:667–673, (1993).
Petit, et al, *Cancer Res.*, 48:1676–1679 (1988).
von Roemeling et al, *Advances in Chronobiology*, Part B, 357–373 (1987).
Cooper et al, *Cancer Res.*, 32:390–397 (1972).
Gentry et al, *Cancer Res.* 31:909–912 (1971).
Bakkeren et al, *Clinica Chimica Acta*, 140:246–247 (1984).
Tuchman et al, *N. Engl. J. Med.*, 313:235–249 (1985).
Diasio et al, *J. Clin, Invest.*, 81:47–51 (1988).
Wadman et al, *Adv. Exp. Med. Biol.*, 165A:109–114 (1984).
Chauduri et al, *Cancer Res.*, 18:318–328 (1958).
Heidelberger et al, *Cancer Res.*, 30:1549–1569 (1970).
Mukherjee et al, *J. Biol. Chem.*, 235:433–437 (1960).
Monks et al, *Biochem. Pharmac.*, 32, 2003–2009 (1983).
Darnowski et al, *Cancer Res.*, 45:5364–5368 (1985).
Cretton et al, *Molec. Pharmac.*, 39:258–266 (1991).
Sommadossi et al, *Antimicrob. Agents Chemother.*, 32, 997–1000 (1988).
Niedzwicki et al, *Biochem Pharmac.*, 31:1857 (1982).
Naguib et al, *Biochem Pharmac.*, 36:2195 (1987).
Naguib et al, *Bichem Pharmac.*, 46:1273–1283 (1993).
Gougoan et al., *J. Med. Chem.* 1991, vol. 34, No. 11, pp. 3305–3309.

(List continued on next page.)

*Primary Examiner*—Mukund J. Shah
*Assistant Examiner*—Sabiha N. Qazi
*Attorney, Agent, or Firm*—Nutter, McClennen & Fish, LLP

[57] ABSTRACT

Novel compounds are provided that are effective to inhibit the activity of DHUDase or UrdPase. Such compounds have the general formula

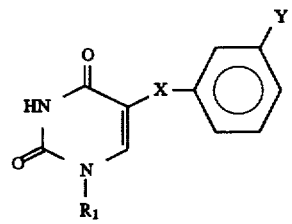

or

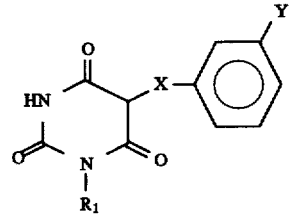

where X is S or Se; Y H is I, F, Cl, Br, methoxy, benzyl, selenenylphenyl, or thiophenyl, and $R_1$ is H or an acyclo tail having the general formula

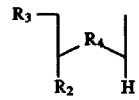

where $R_2$ is H, $CH_2OH$ or $CH_2NH_2$; $R_3$ is OH, $NH_2$, or $OCOCH_2CH_2CO_2H$; and $R_4$ is O, S, or $CH_2$.

The compounds can be used in pharmaceutical compositions, along with various chemotherapeutic agents to increase the efficacy of the treatment. These compounds can also be used in methods of treating patients by coadministering or sequentially administering the enzyme inhibiting compounds with a chemotherapeutic agent effective to treat cancers, or viral, fungal, bacterial, or parasitic infections. The compounds have further utility in enhancing imaging. Further, they can be administered alone to prevent and/or treat disorders of pyrimidine catabolism and other physiological disorders.

20 Claims, No Drawings

OTHER PUBLICATIONS

Heidelberger C., Cancer Research 30, pp. 1549–1569, Jun. 1970.

Darnowski et al., Cancer Research 45, pp. 5364–5368, Nov. 1985.

Cooper et al., Cancer Research 32, pp. 390–397, Feb. 1972.

Gentry et al., Cancer Research 31, pp. 909–912, Jun. 1971.

Roemeling et al., Advances in Chronobiolology, Part B, pp. 357–373, 1987.

Sommadossi et al., Antimicrobial Agents and Chemotherapy, pp. 997–1001, Jul. 1988.

Neidzwicki et al., Biochemical Pharmacology, vol. 31, No. 10, pp. 1857–1861, 1982.

Tuchman et al., Medical Intelligence, vol. 313, No. 4, pp. 245–249, Jul. 1985.

Mukherjee et al., The Journal of Biological Chemistry, vol. 235, No. 2, pp. 433–437, 1960.

ENZYME INHIBITORS, THEIR SYNTHESIS, AND METHODS FOR USE

This is a divisional of copending application Ser. No. 08/146,838 filed on Nov. 2, 1993, U.S. Pat. No. 5,476,855.

BACKGROUND OF THE INVENTION

The invention relates to novel enzyme inhibiting compounds, their synthesis, and their use in treating pathological and physiological conditions.

Pyrimidine analogs and pyrimidine nucleosides are widely used as chemotherapeutic agents for cancer and for viral, fungal, bacterial and parasitic infections. Most pyrimidine analogs used in cancer chemotherapy must be converted to the nucleoside 5'-monophosphate level before any anticancer activity can be realized. However, almost all are administered as nucleosides or bases to facilitate transport into cells. The administered compounds are subject to catabolism and inactivation by various enzymes within a patient's body. Pyrimidine, for example, are degraded by the enzymes uridine phosphorylase (UrdPase) and dihydrouracil dehydrogenase (DHUDase). As a result, the balance between the anabolic (activation) and catabolic (inactivation) pathways must be considered when designing or choosing a chemotherapeutic regime for treating various malignancies, or for treating viral, fungal, bacterial or parasitic infections.

Until recently, most studies of pyrimidine analog metabolism have focused on anabolism, with little attention devoted to catabolism. Pyrimidine bases and nucleoside analogs can be anabolized within a patient's body to the nucleoside 5'-monophosphate, or catabolized to β-amino acids. The catabolism of nucleosides to bases proceeds by nucleoside phosphorylases. The resulting bases are then converted to their respective β-amino acids by a chain of three reactions, catalyzed by DHUDase, dihydropyrimidinase and β-ureidopropionase. Wastemack, *Pharmac. Ther.*, 8:629–651 (1981); Naguib, et al, *Cancer Res.*, 45:5405–5412 (1985). Cytidine, cytosine and their analogs must be deaminated before they can be catabolized.

The importance of DHUDase as a target for chemotherapy has been established by several recent studies. For example, patients receiving continuous infusion of 5-fluorouracil (5-FUra) at a constant rate were found to have plasma concentrations of 5-FUra that varied significantly during treatment. This variation followed a circadian rhythm which was the inverse of that observed for DHUDase activity. Harris et al, *Biochem. Pharmac.*, 37: 4759–4762 (1988); Harris et al, *Cancer Res.*, 49:6610–6614 (1989); Petit E., et al *Cancer Res.*, 48:1676–1679 (1988); Naguib et al, *Biochem. Pharmac.*, 45:667–673, (1993). That is, high plasma concentration of 5-FUra was associated with low DHUDase activity and vice versa. A significant correlation between the circadian rhythm of DHUDase activity and that of the anticancer efficacy of 5-FUra and 5-fluoro-2'-deoxyuridine (5-FdUrd) has also been reported. Petit et al, *Cancer Res.*, 48:1676–1679 (1988); von Roemeling et al, *Advances in Chronobiology*, Part B, 357–373 (1987). Thus it is clear that a strong association exists between the level of DHUDase activity and the bioavailability and efficacy of fluoropyrimidines for chemotherapy.

The importance of DHUDase in cancer chemotherapy is further emphasized by studies with inhibitors of DHUDase, where the inhibitors were found to increase the concentration and half life of 5-FUra in plasma and to dramatically enhance the chemotherapeutic efficacy of 5-FUra in vitro and in vivo. Nevertheless, to administration of known inhibitors of DHUDase with 5-FUra has not been popular due to several drawbacks associated with such previously known inhibitors. Although the known inhibitors enhanced the antitumor activity of 5-FUra, they also served as alternate substrates and caused substantial host-toxicity. Cooper et al, *Cancer Res.*, 32:390–397 (1972); Gentry et al, *Cancer Res.*, 31:909–912 (1971). It was also believed that DHUDase inhibition would mimic the genetic deficiency of this enzyme which is known to be accompanied by neurological disorders. Bakkeren et al, *Clinica Chimica Acta*, 140:246–247 (1984); Tuchman et al *N. Engl. J. Med.*, 313:245–249 (1985); Diasio et al, *J. Clin. Invest.*, 81:47–51 (1988); Wadman et al, *Adv. Exp. Med. Biol.*, 165A: 109–114 (1984). Finally, it was generally believed that tumors lack or possess very little DHUDase activity. Chaudhury et al, *Cancer Res.*, 18:318–328 (1958); Heidelberger et al, *Cancer Res.*, 30:1549–1569 (1970); Mukherjee et al, *J. Biol. Chem.*, 235:433–437 (1960).

Thus, despite the potential promise of DHUDase inhibitors for chemotherapy regimes, currently known inhibitors have demonstrated several drawbacks that have discouraged their use in such treatments.

UrdPase inhibitors are also known to possess a number of clinically useful attributes. For example, UrdPase inhibitors have been proposed to increase the selectivity and efficacy of various uracil and uridine derivatives in cancer chemotherapy. U.S. Pat. No. 5,077,280 (Sommadossi et al) discloses that UrdPase inhibitors can be used as rescue agents to reduce the toxicity of antiviral agents such as 3'-azido-3'-deoxythymidine (AZT). Ideal UrdPase inhibitors are those that are potent, specific, and non toxic. Moreover, useful UrdPase inhibitors should be readily soluble in aqueous solutions buffered within the physiological pH range.

As noted above, halogenated pyrimidine bases such as 5-FUra and halogenated pyrimidine nucleosides such as 5-FdUrd have been used as chemotherapeutic agents in cancer treatments. Because these compounds are subject to rapid degradation, efficacy of the compound is reduced. Also, the catabolites of these chemotherapeutic agents (e.g., 2-fluoro-β-alanine) are believed to be more toxic to a patient's healthy cells.

Halogenated pyrimidine nucleosides, for example, are known to share the same catabolic pathway as uridine. Because there is little functional thyroidine phosphorylase in many tumor cells, the first step in the catabolic pathway in tumor cells relies primarily on UrdPase. The inhibition of this enzyme in tumor cells serves to inhibit the catabolism of the chemotherapeutic agents in tumor tissue, thereby increasing their effectiveness. In healthy host tissue, the halogenated pyrimidine nucleosides can still be catabolized to their pyrimidine counterparts by the action of thymidine phosphorylase.

Similarly, halogenated pyrimidine bases such as 5-FUra can compete with cellular pyrimidines and their nucleotides for incorporation into RNA and DNA. However, UrdPase inhibitors increase the plasma uridine concentration (Monks et al, *Biochem. Pharmac.*, 32, 2003–2009) (1983); Darnowski et al, Cancer Res., 45:5364–5368 (1985)) and the availability of uridine for salvage of host healthy tissue. The increase in plasma uridine concentration also increases the pool of uracil nucleosides in tissue. The increased intracellular uridine concentration can thus reduce the toxicity of halogenated compounds in host tissue. Moreover, it has been shown that the addition of a phosphorylase inhibitor selectively increases the ability of host tissue to salvage uridine.

Darnowski et al, *Cancer Res.*, 45:5364–5368 (1985). This tissue specific enhancement of uridine utilization is of particular importance for chemotherapy regimes using 5-fluorouracil.

Another application of UrdPase inhibitors lies in their use in the protection against host toxicity of various antiviral agents. For example, viral therapies for patients infected with the human immunodeficiency virus (HIV) and/or those suffering from Acquired Immune Deficiency Syndrome (AIDS) have typically involved the administration of an antiviral pyrimidine nucleoside such as AZT. Such an antiviral agent functions by inhibiting the reverse transcriptase enzyme of the HIV to reduce the cytopathic effects of the virus.

The utility of antiviral pyrimidine nucleosides such as AZT has been limited by the toxic effects of AZT or its catabolites such as 3'-amino-3'-deoxythymidine (AMT) on uninfected cells. Cretton et al, *Molec., Pharmac.*, 39:258–266 (1991). Prolonged administration of such compounds produces severe side effects including the suppression of bone marrow growth and severe anemia. The dosage and duration of AZT therapies is limited because of such complications.

It is now known that uridine and, to some extent, cytidine can reverse the toxic effects of AZT in human bone marrow progenitor cells without affecting the antiviral activity of AZT in infected cells. Sommadossi et al *Antimicrob. Agents Chemother.*, 32, 997–1000 (1988). This rescuing effect of uridine, although generally beneficial, has disadvantages because of the body's rapid uridine catabolism. Consequently, high doses are required, and high doses of uridine can cause serious toxic side effects, including phlebitis and pyrogenic reactions.

Viral therapies that combine AZT or similar compounds with UrdPase inhibitors have been suggested in U.S. Pat. No. 5,077,280 (Sommadossi et al). Such treatments utilize UrdPase inhibitors to maintain effective levels of uridine in plasma sufficient to rescue uninfected cells without requiring the administration of high, potentially harmful doses of uridine.

Further, a number of synthetic UrdPase inhibitors have been proposed. See Niedzwicki et al, *Biochem Pharmac.*, 31:1857 (1982); Naguib et al, *Biochem Pharmac.*, 36:2195 (1987); Naguib et al, *Biochem. Pharmac.*, 46:1273–1283 (1993). U.S. Pat. No. 4,613,604 (Chu et al); and U.S. Pat. No. 5,141,943 (Naguib et al). Such UrdPase inhibitors include a variety of substituted acyclouridines and 5-benzyl barbiturate derivatives.

Substituted acyclouridines are good inhibitors of UrdPase, but tend to have limited water solubility and are difficult and expensive to synthesize. Water solubility is essential for practical chemotherapy and treatment of infection in order to enable intravenous administration at physiological pH ranges and to allow formulation of reasonable volumes to be administered. Unfortunately, some acyclouridines, such as benzyl acyclouridine and its derivatives, are soluble only to about 1 mM in water at room temperature. Administration of a physiologically useful dose would require dilution of these compounds into excessively large volumes. 5-Benzyl barbiturate derivatives are also useful UrdPase inhibitors and have been found to be more water soluble and more desirable than derivatives of benzyl acyclouridine.

The maintenance of or increase in plasma uridine levels is also useful to treat several pathological and physiological conditions. For example, uridine has been shown to increase myocardial performance, glucose uptake, glycogen synthesis and the breakdown of ATP in heart tissue of rabbits. Plasma uridine level fluctuations also have important implications in muscle performance and in myocardial contractility. Further, uridine levels are important in central nervous system functioning. For example, the control of intracellular and plasma uridine levels is believed to have important implications in the treatment of CNS disorders, including cerebrovascular disorder and convulsions, epilepsy, Parkinson's and Alzheimer diseases, and senile dementias. Uridine is also potentially useful in the treatment of liver damage and hepatitis. (See Naguib et al, *Biochem. Pharmac.* 46:1273 (1993) and references cited therein).

It is thus apparent that it is desirable to inhibit the enzymes that rapidly degrade certain chemotherapeutic agents or that otherwise contribute to excess uracil or uridine catabolism. In particular, inhibitors of DHUDase and UrdPase are of great relevance to treatment regimes for cancers as well as viral, fungal, bacterial and parasitic infections. Further, the control of and maintenance of plasma uridine levels is thus important in treating and preventing many diseases and pathological conditions. UrdPase inhibitors can also be used to increase available plasma uridine concentrations. As a result, there is a need for new and improved enzyme inhibiting compounds, particularly inhibitors of DHUDase and UrdPase.

Accordingly, it is an object of the invention to provide new compounds useful as DHUDase and UrdPase inhibitors. A further object of the invention is to provide such DHUDase and UrdPase inhibitors which can be used with various chemotherapy regimes to reduce the toxicity of chemotherapeutic agents to normal and uninfected cells. Another object of the invention is to provide methods for increasing the efficacy of chemotherapy regimes in treating cancers as well as viral, fungal, bacterial, and parasitic infections. A further object of the invention is to increase the efficacy of certain chemotherapeutic regimes while reducing adverse patient affects associated with such treatments. Yet another object of the invention is to provide methods for synthesizing such new inhibitors of DHUDase and UrdPase. It is also an object of the invention to provide methods and compositions useful to increase plasma uridine concentrations and effective useful to treat various physiological and pathological conditions. A further object of the invention is to provide methods to treat and/or prevent symptoms of inherited disorders of pyrimidine catabolism. These and other objects of the invention will be apparent from the description that follows.

SUMMARY OF THE INVENTION

The invention relates to novel compounds that are effective as inhibitors of DHUDase or UrdPase. The novel compounds are represented by the formula

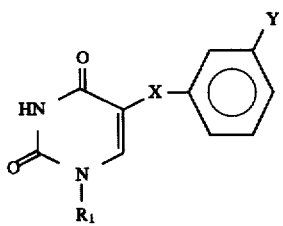

or

-continued

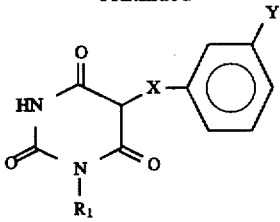

where X is S or Se, Y H is I, F, Cl, Br, methoxy, benzyl, selenenylphenyl, or thiophenyl; and $R_1$ is H or an acyclo tail having the general formula

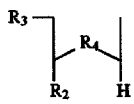

where $R_2$ is H, $CH_2OH$ or $CH_2NH_2$; $R_3$ is OH, $NH_2$ or $OCOCH_2CH_2CO_2H$; and $R_4$ is O, S, or $CH_2$.

Novel compounds of the invention that inhibit DHUDase include 5-(phenylselenenyl)uracil (PSU); 5-(phenylthio) uracil (PTU); 5-(phenylselenenyl)barbituric acid; and 5-(phenylthio)barbituric acid.

Preferred compounds of the invention that inhibit UrdPase include compounds of the above general formulas having an acyclo tail. Such compounds include 1-[(2-hydroxyethoxy)methyl]-5-(phenylselenenyl)uracil (PSAU); 1-[(2-hydroxyethoxy)methyl]-5-(phenylthio)uracil (PTAU); 1-[(2-hydroxyethoxy)methyl]-5-(phenylselenenyl) barbituric acid; and 1-[(2-hydroxyethoxy)methyl]-5-(phenylthio)barbituric acid.

In another embodiment the invention relates to pharmaceutical compositions comprising a chemotherapeutic agent, such as a pyrimidine, in an mount effective to treat cancer or a viral, fungal, bacterial, or parasitic infection; an effective amount of a novel DHUDase or UrdPase inhibitor of the present invention; and a pharmaceutically acceptable carrier. The chemotherapeutic agent can be one that is commonly used to treat cancer or viral, fungal, bacterial or parasitic infections and which is subject to degradation within a patient's body by DHUDase or UrdPase. Examples of such chemotherapeutic agents include pyrimidine compounds such as 3'-azido-3'-deoxythymidine; 3'-fluoro-3'-deoxythymidine; 2', 3'-dideoxycytidin-2'-ene; 3'-deoxythymidin-2'-ene; 3'-azido-2',3'-dideoxyuridine; 2',3'-dideoxy-5-fluoro-3'-thiacytidine; 2',3'-dideoxy-3'-thiacytidine; 5-fluoro-2',3'-dideoxycytidine; 5-fluorouracil; 5-fluoro-2'-deoxyuridine; and heterodimers thereof and enantiomers thereof. The chemotherapeutic agent can also be a prodrug of pyrimidine nucleobase analogs, including 1,(2-tetrahydrofuryl)-5-fluorouracil (TEGAFUR); 5-fluorocytosine; 5'-deoxy-5-fluorouridine; and 1-ethoxymethyl-5-fluorouracil. The chemotherapeutic agent can also be a prodrug sold by Taiho Pharmaceutical Company, Ltd. of Osaka, Japan under the tradename UFT, which is a combination of 1,(2-tetrahydrofuryl)-5-fluorouracil and uracil.

In another embodiment the invention comprises a method for administering chemotherapeutic agents while protecting and/or rescuing normal or uninfected cells from any toxicity that may result from the administration of the chemotherapeutic agent. Further, methods are provided for improving the efficacy of the chemotherapeutic agent. The methods of the invention comprise administering the chemotherapeutic agent, and coadministering or sequentially administering a DHUDase or UrdPase inhibiting compound of the type disclosed herein. The inhibition of the activity of DHUDase or UrdPase prevents or slows the degradation of the chemotherapeutic agent by these enzymes. This prevents or slows the degradation of the chemotherapeutic agent also results in lower levels of potentially toxic catabolites of the chemotherapeutic agent. These methods thus facilitate a higher concentration and/or a longer half-life of the chemotherapeutic agent, thus increasing the efficacy of the treatment regime. An additional benefit is that any toxic side effects of the chemotherapeutic regime are minimized.

The use of enzyme inhibiting compounds of the present invention are also effective to provide increased plasma levels of natural pyrimidines, such as uridine, which can help to protect and/or rescue healthy cells from toxicity induced by chemotherapeutic agents. The administration of these compounds to increase plasma levels of natural pyrimidines can also be effective to treat pathological and physiological disorders that respond to the administration of such pyrimidines. Such disorders responsive to these treatments include CNS disorders, Parkinson's disease, Alzheimer's disease, senile dementia, sleep disorders, muscle dysfunction, lung disorders, diabetes, cardiac insufficiency and myocardial infarction, liver disease and liver damage.

In addition to the novel compounds disclosed herein it has also been discovered that several known compounds are effective as UrdPase inhibitors. The UrdPase inhibiting activity of such compounds was previously unknown.

The present invention also contemplates the synthesis of novel enzyme inhibiting compounds such as 5-(phenylselenenyl)uracil and 5-(phenylthio)uracil.

DETAILED DESCRIPTION OF THE INVENTION

The present invention relates to novel compounds that are effective to inhibit the activity of the enzymes dihydrouracil dehydrogenase (DHUDase) or uridine phosphorylase (UrdPase). These compounds are useful in conjunction with chemotherapeutic regimes that involve the administration of chemotherapeutic agents that are degraded by DHUDase or UrdPase to treat cancer, or viral, bacterial, fungal or parasitic infections. By inhibiting the activity of DHUDase or UrdPase, the compounds of the present invention are effective to slow or prevent the degradation of the chemotherapeutic agent by DHUDase or UrdPase. This results in an increase in the concentration and half-life of the agent and thus increases the efficacy of the agent. Further, by slowing or preventing the degradation of the agents, levels of potentially toxic catabolites of the agent are significantly reduced and toxic side effects associated with many chemotherapeutic regimes are reduced. The DHUDase and UrdPase inhibitors of the invention can also increase intracellular levels of natural pyrimidines (e.g., uridine, cytidine, uracil, and thymine) and can be useful to treat pathological and physiological disorders for which administration of pyrimidines and their nucleotides is known to be effective.

The novel compounds of the invention are represented by the formula

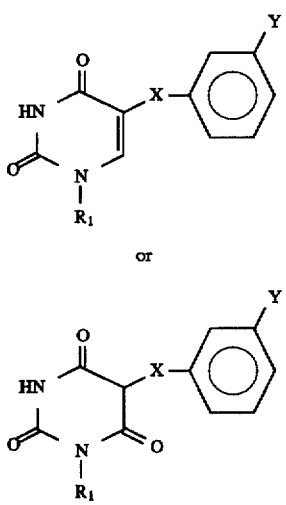

where X is S or Se; Y is I, F, Cl, Br, methoxy, benzyl, selenenylphenyl, or thiophenyl; and $R_1$ is an acyclo tail having the general formula

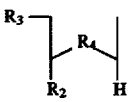

where $R_2$ is H, $CH_2OH$ or $CH_2NH_2$; $R_3$ is OH, $NH_2$, or $OCOCH_2CH_2CO_2H$; and $R_4$ is O, S, or $CH_2$.

Examples of preferred compounds having the above general formula that are effective to inhibit DHUDase include 5-(phenylselenenyl)uracil (PSU); 5-(phenylthio)uracil (PTU); 5-(phenylselenenyl)barbituric acid; and 5-(phenylthio)barbituric acid.

Examples of preferred compounds having the above general formula that are effective as inhibitors of UrdPase include 5-(phenylselenenyl)acyclouridines and 5-(phenylthio)acyclouridines such as 1-[(2-hydroxyethoxy)methyl]-5-(phenylselenenyl)uracil (PSAU) and 1-[(2-hydroxyethoxy)methyl]-5-(phenylthio)uracil (PTAU), respectively. Examples of other preferred UrdPase inhibiting compounds having the above general formula include 1-[(2-hydroxyethoxy)methyl]-5-(phenylselenenyl)barbituric acid and 1-[(2-hydroxyethoxy)methyl]-5-(phenylthio)barbituric acid.

In addition to novel compounds represented by the general formulas shown above other, previously known compounds have been discovered to be effective to inhibit UrdPase. Such compounds include 5-(phenylselenenyl) uridine; 5-(phenylselenenyl)-2'-deoxyuridine; 1-[(2-hydroxyethoxy)methyl]-6-(phenylselenenyl)uridine; 5-(phenylthio) uridine; 5-(phenylthio)-2'-deoxyuridine; and 1-[(2-hydroxyethoxy)methyl]-6-(phenylthio)uridine.

As noted above, many useful chemotherapeutic agents are rapidly catabolized by enzymes such as DHUDase and UrdPase. The rapid degradation of these agents obviously results in lower efficacy of treatments involving such agents as their half-life is reduced. Also, the rapid degradation of these compounds yields catabolites that in many cases can be toxic to host tissue. The invention recognizes that the effectiveness of chemotherapy regimes can be enhanced by using the novel compounds of the invention, and other enzyme inhibiting compounds, in coadministration or sequential administration with various chemotherapeutic agents. By inhibiting the enzymes DHUDase or UrdPase, the compounds of the invention are effective to make more of the chemotherapeutic agent available to a patient for a longer period of time and to minimize or prevent the formation of potentially toxic catabolites.

The enzyme inhibiting compounds of the present invention can be used with a wide variety of chemotherapeutic agents that are effective to treat cancer or to treat viral, fungal, bacterial or parasitic infections. These compounds typically are pyrimidine compounds such as pyrimidine nucleobases, pyrimidine nucleosides, and prodrugs of such compounds. One of ordinary skill in the art will readily appreciate the numerous chemotherapeutic agents, the efficacy of which can be enhanced by the enzyme inhibiting compounds of the invention.

Examples of pyrimidine bases and pyrimidine nucleosides the effectiveness of which can be enhanced by the enzyme inhibitors of the invention include 3'-azido-3'-deoxythymidine; 3'-fluoro-3'-deoxythymidine; 2',3'-dideoxycytadin-2'-ene; 3'-deoxythymidin-2'ene; 5-fluorouracil; 3'-azido-2',3'-dideoxyuridine; 2',3'-dideoxy-5-fluoro-3'-thiacytidine; 2',3'-dideoxy-3'-thiacytidine; 5-fluoro-2',3'-dideoxycytidine; 5-fluoro-2'-deoxyuridine; heterodimers thereof; and enantiomers thereof. Other pyrimidine bases and pyrimidine nucleosides that can be enhanced by the enzyme inhibitors of the invention include prodrugs of pyrimidine nucleobases analogs. Examples of such prodrugs include 1,(2-tetrahydrofuryl)-5-fluorouracil; 5-fluorocytosine; 5'deoxy-5-fluorouridine; and 1-ethoxymethyl-5-fluorouracil. Another suitable prodrug is one sold by Taiho Pharmaceutical Company, Ltd. of Osaka, Japan under the tradename UFT, which combines 1, (2-tetrahydrofuryl)-5-fluorouracil and uracil.

It is also noted that the enzyme inhibiting compounds of the invention are useful with prodrugs such as 5-fluorocytosine that are administered to a patient and can be deaminated to useful chemotherapeutic agent (e.g., 5-fluorouracil) by bacterial or fungal enzymes available within cells through transplanted bacterial or fungal genes.

DHUDase inhibitors, in particular, are effective to prevent or slow the catabolism of various pyrimidine nucleobase analogs (e.g., 5-FUra) or prodrugs of pyrimidine nucleobase analogs (e.g., 1,(2-tetrahydrofuryl)-5-fluorouracil; 5-fluorocytosine; 5'-deoxy-5-fluorouridine; and 1-ethoxymethyl-5-fluorouracil). Such inhibitors also prevent or minimize toxicity (e.g., cardiotoxicity, neurotoxicity, hepatotoxicity, and cholestasis) resulting from toxic catabolites of 5-FUra and its prodrugs (e.g., fluoro-β-alanine and its bile acid conjugates). The DHUDase inhibitors can also be effective to prevent and treat symptoms of inherited disorders of pyrimidine base catabolism that result from increased production of 1,3-alanine and its metabolites. Such disorders include hyper-β-alaninemia, hypercarnosinuria, and β-alauinuria.

UrdPase inhibitors, in particular, are useful to increase plasma uridine levels to prevent or minimize toxicity of chemotherapeutic agents used to treat cancer as well as those used to treat viral, fungal, bacterial, and parasitic infections. The increase of plasma uridine levels can be useful because suitable plasma uridine levels are effective to prevent and/or rescue normal or uninfected host cells from toxicity associated with the administration of many chemotherapeutic agents such as pyrimidine nucleobases and pyrimidine nucleosides. The UrdPase inhibitors can be used alone to increase plasma uridine levels and/or plasma levels of other natural pyrimidines. Alternatively, they can be used in combination with uridine, cytidine, prodrugs or uridine or cytidine, prodrugs of uridine or cytidine nucleosides, and nucleoside transport inhibitors to increase plasma levels of natural pyrimidines such as uridine. The UrdPase inhibitors also prevent or slow the degradation by UrdPase or various anticancer chemotherapeutic agents and chemotherapeutic agents used to treat viral, fungal, bacterial, and parasitic infections. Further, UrdPase inhibitors can prevent or slow the degradation of radiosensitizing drugs to enhance imaging capabilities. Examples of such radiosensitizing drugs include 5-iodo-2'-deoxyuridine and 5-bromo-2'-deoxyuridine.

In another aspect of the invention DHUDase and UrdPase inhibitors of the type noted herein are useful, by themselves, to increase levels of natural pyrimidines such as uridine, cytidine, uracil and thymine. Such treatments can be effective to treat pathological and physiological disorders where administration of pyrimidines (e.g., cytidine, uridine and their nucleotides) are useful. Such disorders include CNS disorders, Parkinson's disease, Alzheimer's disease, senile dementia, sleep disorders, muscle dysfunction, lung disorders, diabetes, cardiac insufficiency and myocardial infarction, liver disease, and liver damage. Further details concerning the increase of plasma uridine levels to treat such disorders are included in copending U.S. patent application Ser. No. 106,225, filed Aug. 13, 1993, which is hereby incorporated by reference.

U.S. Pat. Nos. 5,077,280 and 5,141,943, both of which are incorporated by reference herein, describe various uses of other UrdPase inhibitors. The uses for the UrdPase inhibitors described in these patents are also applicable to the UrdPase inhibitors described herein.

The enzyme inhibiting compounds of the present invention have been found to be more lipophilic than previously known enzyme inhibitors such as acyclouridines and benzyl barbiturates. Consequently, the beneficial, enzyme inhibiting effects of these compounds can be more rapidly directed to the liver, the primary site of pyrimidine metabolism within the body. The lipophilic nature of these compounds also enables them to remain active within a patient's system for a longer period of time.

The preferred dosages of chemotherapeutic agents are known to those of ordinary skill in the art. The preferred dosages will vary depending upon numerous factors, including the age, weight and health of the patient, and the disease to be treated. The potency and potential toxicity of a chemotherapeutic agent are additional factors that influence the dosage of a particular chemotherapeutic agent. AZT, for example, is used to treat AIDS. This drug is effective to inhibit viral replication when administered in amounts ranging from about 10 mg to about 100 mg per kilogram of body weight per day. Such dosage units are employed so that a total of from about 0.7 to about 7 grams of the compound is administered to a subject of about 70 kg of body weight in a 24 hour period. For example, one presently accepted protocol for administration of the pyrimidine nucleoside AZT calls for 200 mg of AZT to be administered three times per day. The preferred therapeutic dosages of other pyrimidine nucleobases and pyrimidine nucleosides are known to those skilled in the art.

Chemotherapeutic agents of the type noted herein may be coadministered or sequentially administered with the enzyme inhibiting compounds of the invention. The preferred dosages of the enzyme inhibiting compounds of the invention range from about 5 to 500 mg/kg/day. A preferred dosage is about 200 mg/kg per day. One of ordinary skill in the art will appreciate that the dosage of chemotherapeutic agent to be administered to any given patient can be influenced by the efficacy of the enzyme inhibiting compounds administered to the patient.

The dosage regimen of the combination therapies described above obviously may be adjusted to provide the optimum therapeutic response. For example, several divided doses may be administered daily or the dose may be proportionally reduced as indicated by the exigencies of the therapeutic situation.

A decided practical advantage provided by this invention is that the active compounds may be administered in any convenient manner, such as by the oral, intravenous, intramuscular, subcutaneous routes, or by regional infusion.

Pharmaceutical compositions may be prepared by combining a desired chemotherapeutic agent with a desired DHUDase or UrdPase inhibitor of the type disclosed herein.

The active compounds disclosed herein may be orally administered, for example, with an inert diluent or with an assimilable edible carrier. They may also be enclosed in hard or soft shell gelatin capsules, or they may be compressed into tablets, or incorporated directly into food. For oral therapeutic administration, the active compounds may be incorporated with excipients and used in the form of ingestible tablets, bucal tablets, troches, capsules, elixirs, suspensions, syrups, wafers and the like. The amount of active compounds in such therapeutically useful compositions is such that a suitable dosage will be obtained.

Pharmaceutical compositions in the form of tablets, troches, pills, capsules and the like may also contain the following: a binder, such as gum tragacanth, acacia, cornstarch, or gelatin; excipients, such as dicalcium phosphate; a disintegrating agent, such as corn starch, potato starch, aliginic acid and the like; a lubricant, such as magnesium stearate; and a sweetening agent, such as sucrose, lactose or saccharine; and a flavoring agent, such as peppermint, oil or wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compounds, sucrose as a sweetening agent, methyl and propylparabens as preservatives, a dye and a flavoring, such as cherry or orange flavor. Of course, any material used in preparing any dosage unit form should be pharmaceutically pure and substantially non-toxic in the amounts employed. In addition, the active compounds may be incorporated into sustained-release preparations and formulations.

The active compounds may also be prepared in the form of pharmaceutical compositions to be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof, and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. Suitable injectable pharmaceutical forms must be sterile and must be fluid to the extent that easy syringability exists. They must be stable under the conditions or manufacture and storage and must be preserved against the contaminating action of microorganisms, such a bacteria and fungi. The carrier can be a solvent or dispersion medium containing for example, water, ethanol, glycerol, propylene glycol, and polyethylene glycol, and vegetable oils. The proper fluidity can be maintained, for example, by the use of a coating such as a lecithin, by the maintenance of the required particle size in the case of dispersions, and by the use of surfactants. Various antibacterial and antifungal agents (e.g., parabens, chlorobutanol, phenol, sorbic acid, thimerosal) can be used to prevent the action of microorganisms. In many cases, it will be preferable to include isotonic agents, for example, sugars or sodium chloride. Prolonged absorption of the injectable compositions can be brought about by the use in the compositions of agents that delay absorption, for example, aluminum monostearate and gelatin.

Sterile injectable solutions can be prepared by incorporating the active compounds in the required amount in the appropriate solvent with various of the other ingredients enumerated above, as required, followed by filtered sterilization. Generally, dispersions can be prepared by incorporating the various sterilized active ingredients into a sterile vehicle which contains the basic dispersion medium and the required additional ingredients of the type enumerated above. Sterile powders used to prepare sterile injectable solutions can be prepared by vacuum-drying and freeze-drying techniques.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art.

5-(Phenylselenenyl)uracil (PSU), 5-(phenylthio)uracil (PTU) and their derivatives can be prepared through a multistep synthesis scheme. A preferred starting compound is 5-bromouracil which is reacted with excess $POCl_3$ to yield 2,4-dichloro-5-bromopyrimidine. When this compound is treated with sodium benzylate, preferably in toluene, at room temperature, it yields 5-bromo-2,4-bis(benzyloxy) pyrimidine. Lithiation of the 5-bromopyrimidine derivative below -80° C. in dry THF with n-BuLi (1.1 equiv.) generated a C-5 lithiated species. The lithiated species can be reacted with either diphenyl diselenide (to obtain PSU) or with dephenyl disulfide (to obtain PTU) (2 equiv.), at a temperature of approximately −75° C. for about ½ hour. Quenching the reaction mixture with glacial AcOH, followed by silica gel column chromatography, providing the corresponding 5-heteraphenyl-2,4-bis(benzyloxy)pyrimidines in 70 to 75 percent yield. The protecting benzyl groups can be readily cleaved by exposure to trimethylsilyl iodide (2.4 equiv.) in dry $CH_2Cl_2$ at room temperature to give the desired 5-(heteraphenyl)uracils, either PSU or PTU, in 78 to 80% yield.

5-phenylselenenyl acyclic nucleosides can be conveniently prepared by direct electrophilic addition of phenylselenenyl chloride to the acyclic nucleosides in dry pyridine at temperatures above more temperature, preferably at about 60° C. Such synthesis methods are described Schinazi et al, J. Med. Chem., 29:1293–1295 (1986), the disclosure of which is hereby incorporated by reference. The products of the electrophilic addition, obtained as white crystalline compounds, are readily purified by chromatography.

The synthesis of these compounds and their utility as enzyme inhibitors is further described below in Examples 1–9.

EXAMPLE 1

(Synthesis of 5'(Phenylselenenyl)-2,4-bis(benzyloxy) pyrimidine)

To a solution of 5-bromo-2,4-bis(benzyloxy)pyrimidine (742 mg, 2 mmol) in dry THF (10 mL) at −80° C. was added dropwise n-BuLi (1.6 M, 1.5 mL, 2.4 mmol) with stirring under an argon atmosphere. After the mixture was stirred for 15 min, diphenyl diselenide (1.25 g, 4 mmol) dissolved in THF (10 mL) was added and the temperature was maintained below −70° C. After 1 h. at that temperature, the reaction mixture was quenched with glacial AcOH (0.5 mL), and the solution was allowed to warm to room temperature. The solution was concentrated to dryness in vacuo, and the residue was purified by silica gel column chromatography using hexane: $CH_2Cl(6:4)$ as eluent to yield a white solid which was crystallized from EtOH to give white needles of 5-phenylselenenyl-2,4-bis(benzyloxy)-pyrimidine (778 mg, 87%); m.p. 66°–68° C.; $^1H$ NMR $(CDCl_3)\delta5.38$ and 5.42 (2 s, 4H, $CH_2$), 7.23–7.49 (m, 15H, 2 Ph and SePh), 8.26 (s, 1H, 6-H). Anal. $(C_{24}H_{20}N_2O_2Se)$ C, H, N.

EXAMPLE 2

(Synthesis of 5-Phenylselenenyluracil (PSLD)

To a solution of 5-phenylselenenyl-2,4-bis(benzyloxy)-pyrimidine (447 mg, 1 mmol) in dry $CH_2Cl_2$ (10 mL) was added trimethylsilyl iodide (520 mg, 2.6 mmol) under anhydrous conditions at room temperature. The yellow solution was stirred for 1 h. The excess trimethylsilyl iodide was destroyed and the intermediate trimethylsilyl ethers formed during the reaction were hydrolyzed by addition of MeOH. The precipitate was filtered and the solid crystallized from EtOH to give pure PSU (210 mg, 78%); m.p. 249°–251° C.; $^1HNMR$ (DMSO-$d_6$) $\delta7.16$–7.37 (m, 5H, SePh), 7.93 (s, 1H, 6-H), 11.28 and 11.39 (2 s, 2H, 2 NH, $D_2O$ exchangeable). Anal. $(C_{10}H_8N_2O_2Se)$ C, H, N.

EXAMPLE 3

(Synthesis of 5-(Phenylthio)-2,4-bis(benzyloxy)pyrimidine)

Reaction of 5-bromo-2,4-bis(benzyloxy)-pyrimidine (742 mg, 2 mmol) sequentially with n-BuLi (1.6 M, 1.5 mL, 2.4 mmol) and diphenyl disulfide (872 mg, 4 mmol) as described in Example 2 yielded the title compound (630 mg, 79%); m.p. 61°–63° C.; $^1H$ NMR $(CDCl_3)$ $\delta5.41$ and 5.45 (2 s, 4H, $CH_2$), 7.06–7.48 (m, 15H, 2 Ph and SPh), 8.37 (s, 1H, 6-H). Anal. $(C_{24}H_{20}N_2O_2S)$ C, H, N.

EXAMPLE 4

(Synthesis of 5-(Phenylthio)uracil (PTU))

Reaction of 5-(phenylthio)-2,4-bis(benzyloxy)pyrimidine (400 mg, 1 mmol) with trimethylsilyl iodide (520 mg, 2.6 mmol) in $CH_2Cl_2$ (15 mL) as described in Example 2 gave 5-phenylthiouracil (160 mg, 72%); m.p. 269°–271° C. (lit.[37] m.p. 272° C.);$^1H$ NMR (DMSO-$d_6$) $\delta7.04$–7.25 (m, 5H, SPh), 7.86 (s, 1H, 6-H),1 1.32 and 11.41 (2s, 2H, 2 NH, $D_2O$ exchangeable).

EXAMPLE 5

(Synthesis of 6-(Phenylselenenyl)-2,4-bis(benzyloxy) pyrimidine)

Reaction of 6-bromo-2,4-bis-(benzyloxy)pyrimidine (742 mg, 2 mmol) sequentially with n-BuLi (1.6 M, 1.5 mL, 2.4 mmol) and diphenyl diselenide (1.25 g, 4 mmol); as described in Example 2, yielded the title compound (590 mg, 66%); m.p. 97°–99° C.; $^1HNMR$ $(CDCl_3)$ $\delta5.28$ and 5.39 (2 s, 4H, $CH_2$), 6.00 (s, 1H, 5-H), 7.26–7.74 (m, 15H, 2 Ph and SePh). Anal. $(C_{24}H_{20}N_2O_2Se)$ C, H, N.

EXAMPLE 6

(Synthesis of 6-phenylselenenyl)uracil)

Reaction of 6-(phenylselenenyl)-2,4-bis(benzyloxy) pyrimidine (447 mg, 1 mmol) with trimethylsilyl iodide (520 mg, 2.6 mmol) in $CH_2Cl_2$ (15 mL), as described in Example 2, gave the desired product (215 mg, 80%); m.p. 238°–240° C.; $^1H$ NMR (DMSO-$d_6$) δ4.66 (s, 1H, 5-H), 7.43–7.70 (m, 5H, SePh), 11.16 and 11.28 (2 s, 2H, 2 NH, $D_2O$ exchangeable). Anal. ($C_{10}H_8N_2O_2Se$) C, H, N.

EXAMPLE 7

(Synthesis of 6-(Phenylthio)-2,4-bis(benzyloxy)pyrimidine)

Reaction of 6-bromo-2,4-bis(benzyloxy)-pyrimidine (742 mg, 2 mmol) sequentially with n-BuLi (1.6M, 1.5 mL, 2.4 mmol) and diphenyl disulfide (872 mg, 4 mmol), as described in Example 2, yielded the title compound (610 mg, 76%); m.p. 102°–104° C.; $^1H$ NMR (CDCl$_3$) δ 5.32 and 5.40 (2 s, 4H, CH$_2$), 5.83 (s, 1H, 5-H), 7.28–7.60 (m, 15H, 2 Ph and SPh), Anal. ($C_{24}H_{20}N_2O_2S$) C, H, N.

EXAMPLE 8

(Synthesis of 6-(Phenylthio)uracil)

Reaction of 6-(phenylthio)-2,4-bis(benzyloxy)pyrimidine (400 mg, 1 mmol) with trimethylsilyl iodide (520 mg, 2.6 mmol) in $CH_2Cl_2$ (15 mL) as described in Example 2, gave 6-phenylthiouracil (190 mg, 86%), m.p. 266°–267° C.; $^1H$ NMR (DMSO-$d_6$) δ 7.04–7.25 (m, 5H, SPh), 7.86 (s, 1H, 6-H), 11.32 and 11.41 (2 s, 2H, 2 NH, $D_2O$ exchangeable). Anal. ($C_{10}H_8N_2O_2S$) C, H, N.

EXAMPLE 8

(Synthesis of 1-[(2-Hydroxyethoxy)methyl]-5-(phenylselenenyl)uracil (PSAU)

Phenylselenenyl chloride (1.14 g, 6 mmol) was dissolved in dry pyridine (15 mL) and then the 1-[(2-hydroxyethoxy) methyl]uracil (1.0 g, 5.37 mmol) was added. The reaction mixture was stirred at 60° C. for 24 h. The mixture was allowed to cool to room temperature and then concentrated in vacuo to remove pyridine. The residue was coevaporated with benzene (2×10 mL) and then with absolute EtOH (10 mL). The residue was loaded onto a silica gel column and eluted first with CHCl$_3$ to remove residual diphenyl diselenide. The product was then obtained by elution with CHCl$_3$:MeOH (95:5) and the TLC pure fractions were pooled and concentrated. The solid residue was recrystallized from absolute EtOH to yield the desired product as a white crystalline solid (1.4 g, 76%); m.p. 118°–120° C.; $^1H$ NMR (DMSO-$d_6$) δ1.60 (s, 1H, OH, $D_2O$ exchangeable) 3.68–3.74 (m, 4H, OCH$_2$CH$_2$O), 5.17 (s, 2H, NCH$_2$O), 7.26–7.57 (m, 6H, SePh and C-6 H), 8.37 (s, 1H, NH, $D_2O$ exchangeable). Anal. ($C_{13}H_{14}N_2O_4Se$) C, H,N.

EXAMPLE 9

(Synthesis of 1-(Ethoxymethyl)-5-(phenylselenenyl)uracil)

Reaction of phenylselenenyl chloride (1.15 g, 6 mmol) with 1-(ethoxymethyl)uracil (850 mg, 5 mmol) in pyridine (25 mL) as described above in Example 8 yielded the title compound (1.20 g, 74%); m.p. 143°–145° C.; $^1H$ NMR (CDCl$_3$) δ1.20 (t, 3H, CH$_3$CH$_2$O), 3.57 (q, 2H, CH$_3$CH$_2$O), 5.08 (s, 2H, NCH$_2$O), 7.22–7.53 (m, 5H, SePh and C-6 H), 8.94 (s, 1H, NH, $D_2O$ exchangeable). Anal. (Cl$_3$H$_{14}$N$_2$O$_3$Se) C, H, N.

The novel enzyme inhibiting compounds of the invention and other useful enzyme inhibiting compounds were evaluated for their ability to inhibit DHUDase and UrdPase. Further, toxicity of these compounds to host tissue was also assessed. The testing conducted and the data obtained are discussed and presented in the examples and tables that follow.

EXAMPLE 10

Mouse livers were obtained from female Swiss Albino (CD1) mice weighing 20–24 g (Charles River Laboratories, Boston, Mass.). Mice were sacrificed by cervical dislocation and the livers removed, weighed, minced, and homogenized in ice-cold (3:1, v/w) buffer [20 mM potassium phosphate, pH 8.0; 1 mM dithiothreitol (DTT), 1 mM EDTA] using a Polytron homogenizer (Brinkmann Instruments, Westbury, N.J.). The homogenates were centrifuged at 105,000×g for 1 h. at 4° C. The supernatant fluids (cytosol) were collected and used as an enzyme source.

All assays described below were conducted at 37° C. under conditions where enzyme activity was linear with respect to time and enzyme concentration. For each inhibitor, 5 concentrations were used ranging from 8–900 µM. Reactions were started by the addition of extract and stopped by boiling in a water bath for 2 minutes followed by freezing. Precipitated proteins were removed by centrifugation. Substrates were separated from products in the supernatant by TLC and the radioactivity in the spots was determined on a percentage basis using a Berthold LB-2821 Automatic TLC-Linear Analyzer.

Pyrimidine nucleotide phosphorylases (dThdPase and UrdPase)

Nucleoside cleavage was measured isotopically by following the formation of nucleobases from their respective nucleosides as previously described. The reaction mixture contained 20 mM potassium phosphate (pH 8), 1 mM EDTA, 1 mM DTT, 1 mM [2-$^{14}$C]uridine or [2-$^{14}$C] thymidine (56 Ci/mol) and 25 µL cytosol in a final volume of 50 µL. The incubation was terminated after 30 min. Uridine and thyroidine were separated from their respective nucleobases on silica gel TLC plates developed with CHCl$_3$:MeOH:AcOH (90:5:5, v/v/v). The R$_f$ values were uridine, 0.07; uracil, 0.43; thyroidine, 0.14; and thymine, 0.62.

DHUDase

The activity of the enzyme was measured by following the formation of dihydrouracil, carbamyl-β-alanine, and β-alanine from [6-$^{14}$C]uracil, as previously described. The reaction mixture contained 20 mM potassium phosphate (pH 8), 1.0 mM EDTA, 2 mM DTT, 5 mM MgCl$_2$, 25 µM [6-$^{14}$C]uracil (56 Ci/mol), 100 µM NADPH and 25 µL of cytosol in a final volume of 50 µL. The incubation was terminated after 15 min. Uracil, dihydrouracil, carbamyl-β-alanine, and β-alanine were separated on cellulose TLC plates developed in the top phase of a mixture of n-BuOH:H$_2$O ammonia (90:45:15, v/v/v). R$_f$ values were dihydrouracil 0.46; uracil 0.23; β-alanine and carbamyl-β-alanine 0.09. DHUDase activity was determined as the sum of the products dihydrouracil, carbamyl-β-alanine, and β-alanine.

Kinetic studies

Determination and significance of apparent K$_i$ values was performed using uridine (1 mM) and 5 different concentrations of the inhibitor ranging from 50–900 M. Apparent K$_i$ values were estimated from Dixon's plots (1/v vs. [I]) of the data by a computer program with least squares fitting. Apparent K$_i$, values are related to K$_i$ values by the following equation:

Apparent $K_i = K_{is}(1+[S]/K_m)/1+([S]/K_m) (K_{is}/K_{ii})$ where $K_{is}$ and $K_{ii}$ are inhibition constants flat would have been estimated from the replot of slope and intercept, respectively, of a Lineweaver-Burk plots vs. [I]. If a compound is a competitive inhibitor with respect to uridine, $K_{ii}=\infty$ and $K_{is}=K_i$. Therefore, the apparent $\cdot K_i K_i(1+[S])1 K_m$). Thus, for UrdPase from mouse liver which has a $K_m$ value of 66 μM for uridine, the apparent $K_i$, of a competitive inhibitor, measured at uridine concentration of 1 mM, is approximately 16-fold higher than their respective $K_i$ values. It should be noted, however, that we have not characterized the compounds used in this study with regard to the type of inhibition (competitive, noncompetitive, or uncompetitive) or whether they are substrates for the enzyme.

Protein concentrations were determined spectrophotometrically by the method of Bradford using bovine γ-globulin as a standard.

Data obtained are illustrated below in Tables 1 and 2.

TABLE 1

Apparent inhibition constants of different compounds with enzymes isolated from mouse liver.

| Inhibitor | Enzyme (Apparent $K_i$, μM ± S.D.) | |
|---|---|---|
| | UrdPase | DHUDase |
| 5-Phenylselenenyluracil (PSU) | 205 ± 35 | 4.8 ± 0.6 |
| 5-(Phenylselenenyl)uridine | 4.0 ± 0.2 | — |
| 5-(Phenylselenenyl)-2'-deoxyuridine | 5.5 ± 0.6 | — |
| PSAU | 3.8 ± 0.8 | * |
| 1-Ethoxymethyl-5-phenylselenenyluracil | 313 ± 32 | * |
| 5-Phenylthiouracil (PTU) | 744 ± 85 | 5.4 ± 0.6 |
| 6-(Phenylselenenyl)acyclouridine | 19.3 ± 1.5 | — |
| 6-(Phenylselenenyl)acyclo-5-FUrd | 35.0 ± 5.6 | — |
| 5-Benzylacyclouridine (BAU) | 3.1 ± 0.22 | — |

TABLE 2

Inhibition constants ($K_{is}$) of PSAU on hepatic uridine phosphorylase from different species

| Inhibitor | Mouse Liver | Human Liver | Monkey Liver |
|---|---|---|---|
| BAU | 420 ± 40 | 1190 ± 200 | 333 ± 49 |
| PSAU | 163 ± 9 | 340 ± 19 | 128 ± 14 |

$K_{is}$ (in nM) ± standard error of estimation measured at 20 mM inorganic phosphate, 30–700 μM uridine and inhibitor concentrations ranging from 50–900 nM.

EXAMPLE 11

Pharmacokinetics of 1-[(2-hydroxyethoxy)methyl]-5-(phenylselenyl)uracil (PSAU) in CD-1 mice PSAU was injected i.p. into female CD-1 mice. At various time intervals, 250 μl of whole blood were collected from the orbital sinuses from three mice by a heparinized Natelson pipet and placed on ice. The whole blood was then centrifuged for 5 minutes to separate the plasma which was kept in a −20° C. freezer until preparation for analysis by the HPLC.

The pharmacokinetic parameters were estimated by compartmental model-independent methods using a SIPHAR/Base program. The AUC was determined by the trapezoidal rule with extrapolation to time infinity using the terminal disposition slope (K) generated by a weighted nonlinear least-squares regression of an exponential fit of the data, with the weighted square factor set as the reciprocal of the calculated concentration squared. Elimination half-life of uridine was calculated from 0.693/K The total plasma clearance (C1) was calculated by dividing the dose by the AUC and the weight of the mouse. The peak plasma concentration ($C_{max}$) values and time to peak plasma concentration ($T_{max}$) values were observed experimental values. Renal clearance ($CL_R$) of uridine was calculated by dividing the dose by the AUC. The data obtained are illustrated below in Table 3.

TABLE 3

Pharmacokinetics of PSAU in CD-1 Mice

| Dose of PSAU | $C_{max}$ | AUC | CL | $Apt_{1/2}$ | $ApV_d$ | MRT |
|---|---|---|---|---|---|---|
| 30 mg/kg | 100.0 | 96.91 | 0.310 | 0.7 | 0.331 | 1.282 |
| 60 mg/kg | 210.0 | 349.00 | 0.173 | 1.4 | 0.356 | 2.275 |

$C_{max}$ is peak plasma concentration [μM]; AUC is area under the curve (μmol × hr/ml); Cl is total plasma clearance (ml/hr/kg); $Apt_{1/2}$ is elimination half-life (hr); $V_d$ is volume of distribution (L/kg); MRT is mean residence time (hr).

EXAMPLE 12

Effect of PSAU on the Pharmacokinetics of Plasma Uridine in CD-1 mice

PSAU was injected i.p. into female CD-1 mice. At various time intervals, 250 μl of whole blood were collected from the orbital sinuses from three mice by a heparinized Natelson pipet and placed on ice. The whole blood was then centrifuged for 5 minutes to separate the plasma which was kept in a −20° C. freezer until preparation for analysis by the HPLC. The pharmacokinetics were analyzed by the procedures noted in Example 11, and the data obtained are presented in Table 4.

TABLE 4

| Dose of PSAU | Normal Conc. | $C_{max}$ | $T_{max}$ | AUC | CL | $Apt_{1/2}$ | $ApV_d$ | MRT |
|---|---|---|---|---|---|---|---|---|
| 30 mg/kg | 2.58 | 8.1 | 1.2 | 74.95 | 0.408 | 5.3 | 3.032 | 8.045 |
| 60 mg/kg | 3.07 | 14.6 | 2.5 | 113.12 | 0.601 | 7.2 | 4.029 | 11.068 |

Materials

Melting points were determined on an Electrothermal IA 8100 digital melting point apparatus and are uncorrected. $^1$H NMR spectra were recorded on a General Electric QE-300 (300 MHz) spectrometer. Experiments were monitored using TLC analysis performed on Kodak chromatogram sheets precoated with silica gel and a fluorescent indicator, while column chromatography, employing silica gel (60–200 mesh; Fisher Scientific, Fair Lawn, N.J.) was used for the purification of products. Tetrahydrofuran (THF) was freshly distilled from the sodium benzophenone salt. LDA (2.0 M), n-BuLi (1.6 M), diphenyl diselenide, diphenyl disulfide, and trimethylsilyl iodide and other chemicals were purchased from Aldrich Chemical Company (Milwaukee, Wis.). Microanalyses were performed at Atlantic Microlabs (Atlanta, Ga.). [2-$^{14}$C]Uridine (56 Ci/mol), [2-$^{14}$C] thymidine (56 Ci/mol), and [6-$^{14}$C]uracil (56 Ci/mol) were obtained from Moravek Biochemicals Inc., Brea, Calif.; [6-$^{14}$C]orotate (46.9 Ci/mol) from New England Nuclear Research Products, DuPont Co., Boston, Mass.; silica gel G/W$_{254}$ polygram, polyethyleneimine cellulose 300 PEI/UV$_{254}$ and cellulose CEL 300 UV polygram thin layer chromatography plates from Brinkmann, Westbury, N.J.; protein assay kit from Bio-Rad Laboratories, Richmond, Calif. All other chemicals were obtained from Sigma Co., St. Louis, Mo.

It should be clear that various modifications, additions and subtractions can be made without departing from the spirit or scope of the invention. For example, it should be appreciated that the present invention can also be employed in conjunction with other chemotherapeutic agents or biological response-modifying agents. For example, the combination therapy of the present inventions can be employed in tandem with the administration of bone marrow stimulating factors, such as granulocyte-macrophage colony stimulating factors (GM-CFSs), other colony stimulating factors, erythropoietin (EPO) and other compounds that stimulate hematopoietic activity. (For a further discussion of GM-CSF activity, see Hammer et al, *Antimicrobial Agents and Chemotherapy*, 31: 1046–1050 (1987). Similarly, the combination therapy of the present invention can be undertaken in conjunction with efforts to stimulate the immune system, such as by the administration of interferons (e.g., alpha-A inteferon) or other lymphokines.

All references cited above are expressly incorporated by reference herein.

What is claimed is:

1. A pharmaceutical composition comprising a pyrimidine compound in an amount effective to disrupt viral, cancer, fungal, parasite, or bacterial replication;

an enzyme inhibiting compound represented by the formula

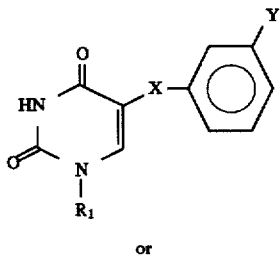

or

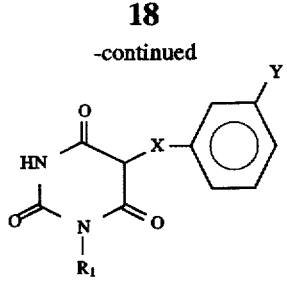

where X is S or Se; Y is H, I, F, Cl, Br, methoxy, benzyl, selenenylphenyl, or thiophenyl; and R$_1$ is H or an acyclo tail having the general formula

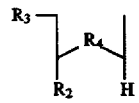

where R$_2$ is H, CH$_2$OH, or CH$_2$NH$_2$; R$_3$ is OH, NH$_2$, or OCOCH$_2$CH$_2$CO$_2$H; and R$_4$ is O, S, or CH$_2$; and a pharmaceutically acceptable carrier.

2. The composition of claim 1 wherein the pyrimidine compound is selected from the group consisting of pyrimidine nucleobase analogs, prodrugs of pyrimidine nucleobase analogs, pyrimidine nucleoside analogs, prodrugs of pyrimidine nucleoside analogs, heterodimers thereof, and enantiomers thereof.

3. The composition of claim 2 wherein the pyrimidine compound is selected from the group consisting of 3'-azido-3'-deoxythymidine; 3'-fluoro-3'-deoxythymidine; 2',3'-dideoxycytidin-2'-ene; 3'-deoxythymidin-2'-ene; 3'-azido-2', 3'-dideoxyuridine; 2',3'-dideoxy-5-fluoro-3'-thiacytidine; 2',3'-dideoxy-3'-thiacytidine; 5-fluoro-2',3'-dideoxycytidine; 5-fluorouracil; 5-fluoro-2'-dexoyuridine; 1,(2-tetrahydrofuryl)-5-fluorouracil; 5-fluorocytosine; 5'-deoxy-5-fluorouridine; 1-ethoxymethyl-5-fluorouracil; heterodimers thereof; and enantiomers thereof.

4. The composition of claim 1 wherein the enzyme inhibiting compound inhibits DHUDase and is selected from the group consisting of 5-(phenylselenenyl)-uracil; 5-(phenylthio)uracil; 5-(phenylselenenyl)barbituric acid; and 5-(phenylthio)barbituric acid.

5. The composition of claim 1 wherein the enzyme inhibiting compound inhibits UrdPase and is selected from the group consisting of 1-(2-hydroxyethoxy)methyl]-5-(phenylselenenyl)uracil; 1-[(2-hydroxyethoxy)methyl]-5-phenylthio)uracil; 1-[(2-hydroxyethoxy)methyl]-5-(phenylselenenyl)barbituric acid; and 1-[(2-hydroxyethoxy) methyl]-5-(phenylthio)barbituric acid.

6. A method for protecting and/or rescuing normal or uninfected cells from toxicity resulting from the administration of a chemotherapeutic agent, comprising administering a chemotherapeutic agent effective to disrupt viral, cancer, fungal, bacterial or parasite replication; and coadministering or sequentially administering an amount of an enzyme inhibiting compound effective to inhibit DHUDase or UrdPase, the compound being represented by the general formula

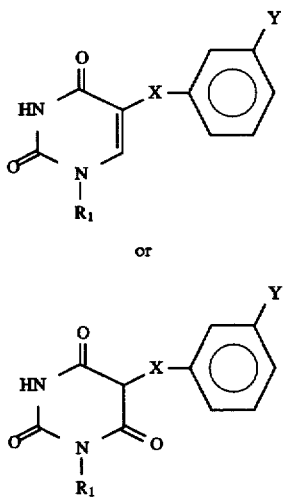

or where X is S or Se; Y is H, F, I, Cl, Br, methoxy, benzyl, selenenylphenyl, or thiophenyl; and $R_1$ is H or an acyclo tail having the general formula

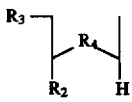

where $R_2$ is H, $CH_2OH$ or $CH_2NH_2$; $R_3$ is OH, $NH_2$, or $OCOCH_2CH_2CO_2H$; and $R_4$ is O, S, or $CH_2$.

7. The method of claim 6 wherein the chemotherapeutic agent is selected from the group consisting of pyrimidine nucleobase analogs, prodrugs of pyrimidine nucleobase analogs, pyrimidine nucleoside analogs, prodrugs of pyrimidine nucleoside analogs, heterodimers thereof, and enantiomers thereof.

8. The method of claim 7 wherein the chemotherapeutic agent is selected from the group consisting of 3'-azido-3'-deoxythymidine; 3'-fluoro-3'-deoxythymidine; 2',3'-dideoxycytidin-2'-ene; 3'-deoxythymidin-2'-ene; 3'-azido-2', 3'-dideoxyuridine; 2',3'-dideoxy-5-fluoro-3'-thiacytidine; 2',3'-dideoxy-3'-thiacytidine; 5-fluoro-2',3'-dideoxycytidine; 5-fluorouracil; 5-fluoro-2'-dexoyuridine; 1,(2-tetrahydrofuryl)-5-fluorouracil; 5-fluorocytosine; 5'-deoxy-5-fluorouridine; 1-ethoxymethyl-5-fluorouracil; heterodimers thereof; and enantiomers thereof.

9. The method of claim 6 wherein the enzyme inhibiting compound inhibits DHUDase and is selected from the group consisting of 5-(phenylselenenyl)uracil; 5-(phenylthio)uracil; 5-(phenylselenenyl)barbituric acid; and 5-(phenylthio)barbituric acid.

10. The method of claim 5 wherein the enzyme inhibiting compound inhibits uridine phosphorylase and is selected from the group consisting of 1-[(2-hydroxyethoxy)methyl]-5-(phenylselenenyl)uracil; 1-[(2-hydroxyethoxy)methyl]-5-(phenylselenenyl) barbituric acid; and 1-[(2-hydroxyethoxy) methyl]-5-(phenylthio)barbituric acid.

11. The method of claim 6 wherein the enzyme inhibiting compound is administered at a dosage of about 5 to 500 mg/kg/day.

12. A method for protecting and/or rescuing normal or uninfected cells from toxicity resulting from the administration of a chemotherapeutic agent, comprising administering an amount of a chemotherapeutic agent effective to disrupt viral cancer, fungal, bacterial or parasite replication; and coadministering or sequentially administering an UrdPase inhibiting compound at a dosage of about 5 to 200 mg/kg/day, the UrdPase inhibiting compound being selected from the group consisting of 1-[(2-hydroxyethoxy)methyl]-5-(phenylselenenyl)uracil; 1-[(2-hydroxyethoxy)methyl]-5-(phenylthio)uracil; 1-[(2-hydroxyethoxy)methyl]-5-(phenylselenenyl)barbituric acid; 1-[(2-hydroxyethoxy)methyl]-5-(phenylthio) barbituric acid; 5-(phenylselenenyl)uridine; 5-(phenylselenenyl)-2'-deoxyuridine; 5-(phenylthio)-2'-deoxyuridine.

13. A method of improving the efficacy of a pyrimidine base or pyrimidine nucleoside therapeutic agent, comprising:

administering a pyrimidine base or a pyrimidine nucleoside therapeutic agent; and coadministering or sequentially administering an enzyme inhibiting compound represented by the general formula

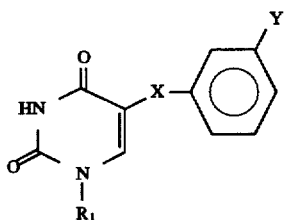

or

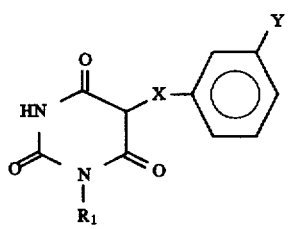

where X is S or Se; Y is H, F, I, Cl, Br, methoxy, benzyl, selenenylphenyl, or thiophenyl; and $R_1$ is H or an acyclo tail having the general formula

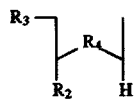

where $R_2$ is H, $CH_2OH$ or $CH_2NH_2$, $R_3$ is OH, $NH_2$, or $OCOCH_2CH_2CO_2H$; and $R_4$ is O, S, or $CH_2$.

14. The method of claim 13 wherein the therapeutic agent is selected from the group consisting of pyrimidine nucleobase analogs, prodrugs of pyrimidine nucleobase analogs, pyrimidine nucleoside analogs, prodrugs of pyrimidine nucleoside analogs, heterodimers thereof, and enantiomers thereof.

15. The method of claim 14 wherein the therapeutic agent is selected from the group consisting of 3'-azido-3'-deoxythymidine; 3'-fluoro-3'-deoxythymidine; 2',3'-dideoxycytidin-2'-ene; 3'-deoxythymidin-2'-ene; 3'-azido-2', 3'-dideoxyuridine; 2',3'-dideoxy-5-fluoro-3'-thiacytidine; 2',3'-dideoxy-3'-thiacytidine; 5-fluoro-2',3'-dideoxycytidine; 5-fluorouracil; 5-fluoro-2'-dexoyuridine; 1-(2-tetrahydrofuryl)-5-fluorouracil; 5-fluorocytosine; 5'-deoxy-5-fluorouridine; 1-ethoxymethyl-5-fluorouracil; heterodimers thereof; and enantiomers thereof.

16. The method of claim 3 wherein the enzyme inhibiting compound inhibits DHUDase and is selected from the group consisting of 5-(phenylselenenyl)-uracil (PSU); 5-(phenylthio)uracil (PTU); 5-(phenylselenenyl)barbituric acid; and 5-(phenylthio)barbituric acid.

17. The method of claim 13 wherein the enzyme inhibiting compound inhibits UrdPase and is selected from the group consisting of 1-[(2-hydroxyethoxy)methyl]-5-(phenylselenenyl)uracil; 1-[(2-hydroxyethoxy)methyl]-5-(phenylthio)uracil; 1-[(2-hydroxyethoxy)methyl]-5-(phenylselenenyl)barbituric acid; and 1-[(2-hydroxyethoxy) methyl]-5-(phenylthio)barbituric acid.

18. The method of claim 13 wherein the enzyme inhibiting compound is administered at a dosage f about 5 to 500 mg/kg/day.

19. A method of improving the efficacy of a pyrimidine base or pyrimidine nucleoside therapeutic agent, comprising administering a pyrimidine base or a pyrimidine nucleoside therapeutic agent; and coadministering or sequentially administering an UrdPase inhibiting compound at a dosage of about 5 to 500 mg/kg/day, the UrdPase inhibiting compound being selected from the group consisting of 1-[(2-hydroxyethoxy)methyl]-5-(phenylselenenyl)uracil; 1-[(2-hydroxyethoxy)methyl]-5-(phenylthio)uracil; 1-[(2-hydroxyethoxy)methyl]-5-(phenylselenenyl)barbituric acid; and 1-[(2-hydroxyethoxy)methyl]-5-(phenylthio) barbituric acid; 5-(phenylselenenyl)uridine; 5-(phenylselenenyl)-2'-deoxyuridine.

20. A method of increasing intracellular levels of pyrimidines to treat pathological or physiological condition that responds favorably to increased pyrimidine levels by administering to a patient a compound of the general formula

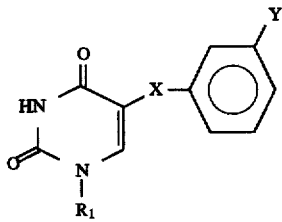

or

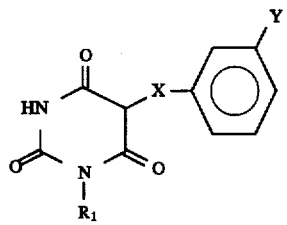

where X is S or Se; Y is H, I, F, Cl, Br, methoxy, benzyl, selenenylphenyl, or thiophenyl; and $R_1$ is H or an acyclo tail having the general formula

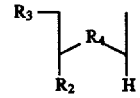

where $R_2$ is H, $CH_2OH$ or $CH_2NH_2$; $R_3$ is OH, $NH_2$, or $OCOCH_2CH_2CO_2H$; and $R_4$ is O, S, or $CH_2$, the compound being administered in an amount effective to increase intracellular pyrimidine levels within the patient.

* * * * *